(12) United States Patent
Laffargue et al.

(10) Patent No.: US 7,927,338 B2
(45) Date of Patent: Apr. 19, 2011

(54) SURGICAL DEVICE FOR IMPLANTING A TOTAL HIP PROSTHESIS

(75) Inventors: Philippe Laffargue, La Madeleine (FR); Henri Migaud, Lille (FR); Jean Puget, Toulouse (FR); François Giraud, Templemars (FR); Jacques Tabutin, Le Cannet (FR)

(73) Assignee: Tornier SAS, Saint Ismier (FR)

( * ) Notice: Subject to any disclaimer, the term of this patent is extended or adjusted under 35 U.S.C. 154(b) by 1390 days.

(21) Appl. No.: 11/054,618

(22) Filed: Feb. 10, 2005

(65) Prior Publication Data
US 2005/0203536 A1 Sep. 15, 2005

Related U.S. Application Data

(60) Provisional application No. 60/543,274, filed on Feb. 11, 2004.

(30) Foreign Application Priority Data

Feb. 10, 2004 (FR) ...................................... 04 01281

(51) Int. Cl.
*A61B 17/58* (2006.01)
*A61B 17/60* (2006.01)
*A61F 2/00* (2006.01)
*A61B 19/00* (2006.01)
*A61B 5/103* (2006.01)
*A61B 5/117* (2006.01)

(52) U.S. Cl. ............... 606/91; 600/595; 606/81; 606/99; 606/130

(58) Field of Classification Search ................... 600/425, 600/426, 595; 382/195; 606/91, 92, 99, 606/130
See application file for complete search history.

(56) References Cited

U.S. PATENT DOCUMENTS

| | | |
|---|---|---|
| 5,171,289 A | 12/1992 | Tornier |
| 5,314,485 A | 5/1994 | Judet |
| 5,326,359 A | 7/1994 | Oudard |
| 5,358,526 A | 10/1994 | Tornier |
| 5,405,399 A | 4/1995 | Tornier |

(Continued)

FOREIGN PATENT DOCUMENTS

WO WO 02/02028 A 1/2002

(Continued)

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner* — Max Hindenburg
*Assistant Examiner* — Adam J Eiseman
(74) *Attorney, Agent, or Firm* — Faegre & Benson LLP

(57) ABSTRACT

The surgical device according to the invention comprises both means for per-operative measurement and for memorization of a plurality of positions of a given femoral prosthetic direction and means for per-operative comparison of these positions with the cone of mobility of the prosthesis to be implanted, the position of the axis of revolution of this cone being, during the implantation of the prosthesis, adjustable with respect to the zone of the pelvis where the implantation of an acetabulum of the prosthesis is provided. By using this device, the surgeon can easily and rapidly determine, in the course of the surgical operation, a preferential direction for implanting the prosthetic acetabulum in order to reduce the subsequent risks of dislocations of the implanted prosthesis.

24 Claims, 4 Drawing Sheets

U.S. PATENT DOCUMENTS

| | | | |
|---|---|---|---|
| 5,429,639 A | 7/1995 | Judet | |
| 5,458,650 A | 10/1995 | Carrett et al. | |
| 5,505,731 A | 4/1996 | Tornier | |
| 5,591,168 A | 1/1997 | Judet et al. | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,766,256 A | 6/1998 | Oudard et al. | |
| 5,824,106 A | 10/1998 | Fournol | |
| 5,871,018 A | 2/1999 | Delp et al. | |
| 5,879,395 A | 3/1999 | Tornier et al. | |
| 5,880,976 A * | 3/1999 | DiGioia, III et al. | 703/7 |
| 6,002,859 A | 12/1999 | DiGioia, III et al. | |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,205,411 B1 | 3/2001 | Digioia, III | |
| 6,206,925 B1 | 3/2001 | Tornier | |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,379,387 B1 | 4/2002 | Tornier | |
| 6,454,809 B1 | 9/2002 | Tornier | |
| 6,488,712 B1 | 12/2002 | Tornier et al. | |
| 6,540,770 B1 | 4/2003 | Tornier et al. | |
| 6,582,469 B1 | 6/2003 | Tornier | |
| 6,599,295 B1 | 7/2003 | Tornier et al. | |
| 6,626,946 B1 | 9/2003 | Walch et al. | |
| 6,711,431 B2 * | 3/2004 | Sarin et al. | 600/426 |
| 6,761,740 B2 | 7/2004 | Tornier | |
| 6,767,368 B2 | 7/2004 | Tornier | |
| 6,802,864 B2 | 10/2004 | Tornier | |
| 6,824,567 B2 | 11/2004 | Tornier et al. | |
| 6,890,357 B2 | 5/2005 | Tornier | |
| 6,969,406 B2 | 11/2005 | Tornier | |
| 7,033,396 B2 | 4/2006 | Tornier | |
| 2002/0077540 A1 | 6/2002 | Kienzle, III | |
| 2003/0009170 A1 | 1/2003 | Tornier | |
| 2003/0009171 A1 | 1/2003 | Tornier | |
| 2003/0028198 A1 | 2/2003 | Tornier et al. | |
| 2003/0153829 A1 | 8/2003 | Sarin | |
| 2003/0212403 A1 | 11/2003 | Swanson | |
| 2004/0117026 A1 * | 6/2004 | Tuma et al. | 623/18.11 |
| 2004/0134821 A1 | 7/2004 | Tornier | |
| 2004/0210220 A1 | 10/2004 | Tornier | |
| 2004/0215200 A1 | 10/2004 | Tornier et al. | |
| 2004/0230197 A1 | 11/2004 | Tornier et al. | |
| 2004/0230199 A1 * | 11/2004 | Jansen et al. | 606/91 |
| 2005/0021044 A1 | 1/2005 | Stone et al. | |
| 2005/0049709 A1 | 3/2005 | Tornier | |
| 2005/0055102 A1 | 3/2005 | Tornier et al. | |
| 2005/0101966 A1 | 5/2005 | Lavallee | |
| 2005/0165490 A1 | 7/2005 | Tornier | |
| 2005/0251026 A1 | 11/2005 | Stone | |
| 2005/0278030 A1 | 12/2005 | Tornier et al. | |
| 2005/0278031 A1 | 12/2005 | Tornier et al. | |
| 2005/0278032 A1 | 12/2005 | Tornier et al. | |
| 2005/0278033 A1 | 12/2005 | Tornier et al. | |
| 2005/0281465 A1 * | 12/2005 | Marquart et al. | 382/195 |
| 2005/0288791 A1 | 12/2005 | Tornier et al. | |
| 2006/0015185 A1 | 1/2006 | Chambat et al. | |
| 2006/0173457 A1 | 8/2006 | Tornier | |
| 2006/0235538 A1 | 10/2006 | Rochetin et al. | |
| 2007/0162142 A1 | 7/2007 | Stone | |
| 2008/0287781 A1 | 11/2008 | Revie et al. | |

FOREIGN PATENT DOCUMENTS

| | | |
|---|---|---|
| WO | WO 02/080824 A | 10/2002 |
| WO | WO 2004/001569 A | 12/2003 |

OTHER PUBLICATIONS

Rochetin et al., U.S. Appl. No. 11/401,415, entitled "Surgical Apparatus for Implantation of a Partial or Total Knee Prosthesis," filed Apr. 11, 2006.

Rochetin, U.S. Appl. No. 11/670,274, entitled "Offset Stem Tibial Implantation," filed Feb. 1, 2007.

Ratron et al., U.S. Appl. No. 11/626,735, entitled "Surgical Instrumentation Kit for Inserting an Ankle Prothesis," filed Jan. 24, 2007.

* cited by examiner

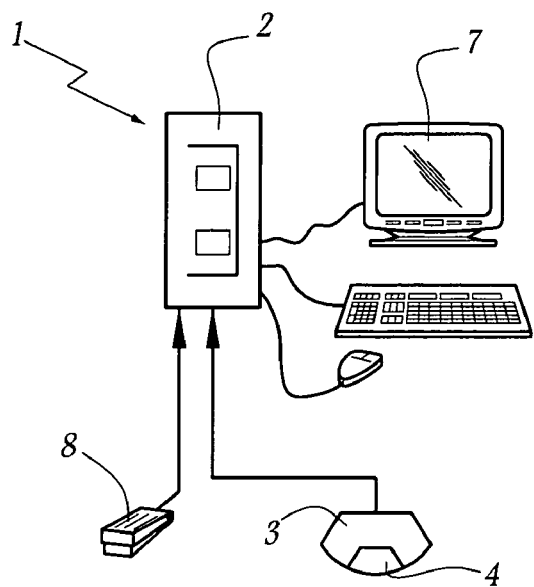
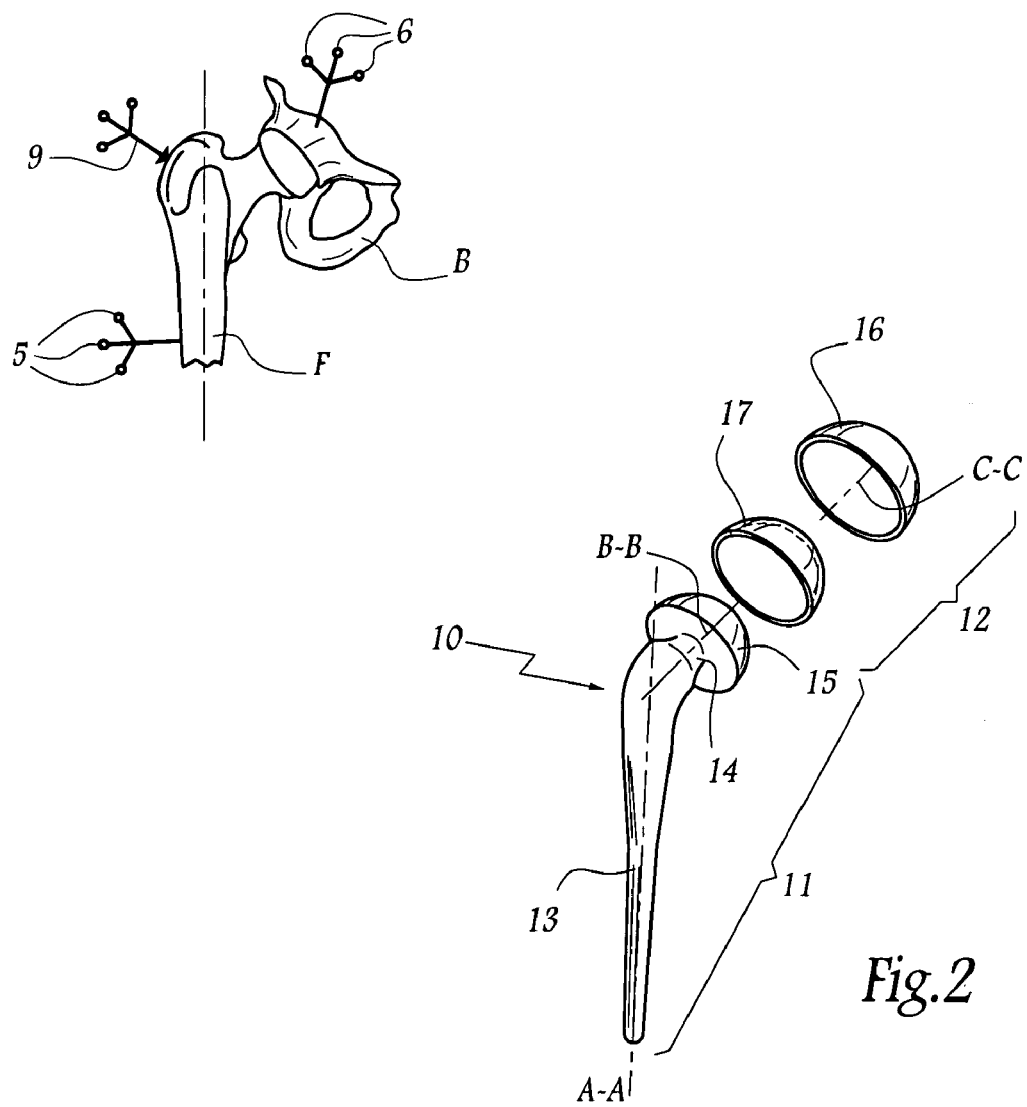
Fig.1
Fig.2

SURGICAL DEVICE FOR IMPLANTING A TOTAL HIP PROSTHESIS

CROSS REFERENCE TO RELATED APPLICATIONS

This application claims priority from U.S. Provisional Patent Application, Ser. No. 60/543,274 which was filed on Feb. 11, 2004 with the same inventors and title.

FIELD OF THE INVENTION

The present invention relates to a surgical device for implanting a total hip prosthesis.

BACKGROUND OF THE INVENTION

A total hip prosthesis conventionally comprises, on the one hand, a femoral part constituted by a stem, at one end of which is fixed a femoral head defining a globally spherical convex articular surface and, on the other hand, a cotyloid part to be fixed to the bone of the pelvis, comprising for example a cotyloid metal cup in hemispherical form, inside which is housed an insert made of plastics material or ceramics in which the femoral head is articulated.

When such a total hip prosthesis is fitted, the surgeon implants, on the one hand, the femoral stem inside a cavity hollowed out longitudinally in the bone of the femur and, on the other hand, the cotyloid part of the prosthesis in a globally hemispherical cavity hollowed out in the bone of the pelvis. The direction of implantation of the femoral stem in the bone of the femur is globally imposed by the elongated shape of the femur bone, while the surgeon has greater liberty to choose the position of implantation of the cotyloid part in the cavity hollowed out in the pelvic bone. The choice of this position has a direct influence on the position of the axis of revolution of the theoretical cone of mobility of the implanted prosthesis, this axis of revolution corresponding in fact to the axis of revolution of the hemispherical cup connected to the pelvic bone.

It has been noted that the positioning of the acetabulum at the level of the zone of implantation of the pelvis has an effect on the mechanical behaviour of the implanted prosthesis. More precisely, when the prosthesis is articulated in movements of extreme amplitude, particularly in movements combining elementary displacements of the hip in flexion/extension, in abduction/adduction and/or in medial rotation/lateral rotation, it may happen that it is urged outside the cone of mobility of the prosthesis, in that case provoking a bearing contact between the femoral neck of the prosthesis and the edge of the acetabulum. Under these conditions, the prosthesis may be dislocated.

U.S. Pat. No. 6,205,411 proposes a method for fitting a hip prosthesis which assists the surgeon in implanting the prosthesis with a view to limiting the risks of subsequent dislocations of the prosthesis by adapting it to the anatomy of the patient treated. To that end, it is provided to use, on the one hand, a pre-operative simulator of the biomechanical kinematics of the patient's hip provided in virtual manner with the prosthesis to be subsequently implanted and, on the other hand, a device for per-operative guiding of the surgeon's gestures to fit the prosthesis, this device being controlled from the results issuing from the biomechanical simulation carried out by the simulator. To allow the simulator to determine an adequate positioning of the prosthesis to be implanted, it is necessary to provide it with a complete and detailed mapping of the patient's bone structure, particularly by means of non-invasive tomographic techniques. All these data are processed by computer in order to re-create the patient's osseous anatomy virtually, and then, still pre-operatively, to simulate its behaviour with a virtual prosthesis. This method therefore necessitates very considerable data processing means which are expensive, as well as a large amount of pre-operative data, which prolongs the duration and cost of hospitalization of the patient.

It is an object of the present invention to propose a surgical device which assists the surgeon more simply, more rapidly and more economically during the procedure of implanting a total hip prosthesis, with a view to limiting the risks of subsequent dislocations of the prosthesis, by being adapted as best possible to the anatomy of each patient treated.

SUMMARY OF THE INVENTION

In that spirit, the invention relates to a surgical device for implanting a total hip prosthesis, characterized in that it comprises means for per-operative measurement and for memorization of a plurality of positions of a given femoral prosthetic direction and means for per-operative comparison of these positions with the cone of mobility of the prosthesis to be implanted, the position of the axis of revolution of this cone being, during the implantation of the prosthesis, adjustable with respect to the zone of the pelvis where the implantation of an acetabulum of the prosthesis is provided.

By using the device according to the invention, the surgeon may, during the surgery proper, compare the cone of mobility of the prosthesis associated with the prosthesis to be implanted with the different measured positions of the femoral prosthetic direction considered, these positions preferably corresponding to extreme articular configurations of the operated patient's hip, namely articular configurations combining the movements of flexion/extension, of abduction/adduction and/or of medial/lateral rotation, such as for example the cross-legged configuration which combines the movements of flexion, of abduction and of lateral rotation. During the surgical operation of fitting the prosthesis, the surgeon then chooses a preferential direction to implant the acetabulum of the prosthesis, allowing the subsequent manipulation of the prosthesis up to in these extreme articular configurations without risking dislocation thereof. In other words, the surgical device according to the invention allows the surgeon to determine this preferential direction of implantation, or a plurality of these preferential directions, that the surgeon will then respect at the end of the surgical operation to implant the acetabulum of the prosthesis.

According to other characteristics of this device, taken separately or in any technically possible combinations:
  it comprises means for communicating to the surgeon the comparison between the positions of the femoral prosthetic direction and the cone of mobility of the prosthesis,
  the communication means comprise a means for displaying symbolic representations of the positions of the femoral prosthetic direction and of the position of the cone of mobility of the prosthesis,
  it comprises means for selection by the surgeon or for calculation and memorization of at least one preferential position of the axis of the cone of mobility of the prosthesis,
  it further comprises, on the one hand, an impactor for definitively positioning the acetabulum of the prosthesis in the zone of implantation of the pelvis, equipped with means for locating in space and, on the other hand, means for comparing the direction of impaction of this impactor with the preferential position, the measuring means comprise a phantom femoral component defining the femoral prosthetic direction, positions of this femoral component with respect to the zone of implantation of the pelvis corresponding to the positions of the femoral prosthetic direction to be compared with the cone of mobility of the prosthesis, it comprises means for determining the centre of an osseous cavity of the pelvis, constituting the zone of implantation of the pelvis and adapted to receive the phantom femoral component when the different positions of this component are measured, it comprises a support for the phantom femoral component, adapted to be fixedly connected to the femur and to bear means for locating in space, this support being for example constituted by all or part of a femoral rasp, a femoral pin or a prosthetic stem, the phantom femoral component defines an articular surface adapted to be directly articulated on the zone of implantation of the pelvis and substantially identical to the outer surface of the acetabulum of the prosthesis to be implanted, it comprises a phantom acetabulum reproducing the axis of the cone of mobility of the prosthesis and equipped with a means for manual manipulation with respect to the zone of implantation of the pelvis, provided with means for locating in space.

The invention also relates to a surgical method for implantation of a total hip prosthesis, in which, per-operatively and successively:

the bone of the femur and the bone of the pelvis of a patient to be treated are located in space, a plurality of positions of a given femoral prosthetic direction with respect to a cavity of the pelvis are measured and memorized, these measured positions are compared with the cone of mobility of the prosthesis to be implanted, the position of the axis of revolution of this cone being adjusted with respect to the cavity in the course of the surgical operation, at least one preferential position of this axis of revolution is determined, and a cotyloid part of the prosthesis is impacted in the cavity of the pelvis in said preferential position.

BRIEF DESCRIPTION OF THE DRAWINGS

The invention will be more readily understood on reading the following description given solely by way of example and made with reference to the accompanying drawings, in which:

FIG. 1 is a schematic view of a part of a surgical device according to the invention, applied to the hip of a patient to be operated on.

FIG. 2 is an exploded view in perspective of a total hip prosthesis to be implanted by means of the device of FIG. 1.

DESCRIPTION OF PREFERRED EMBODIMENT

Figure 3:
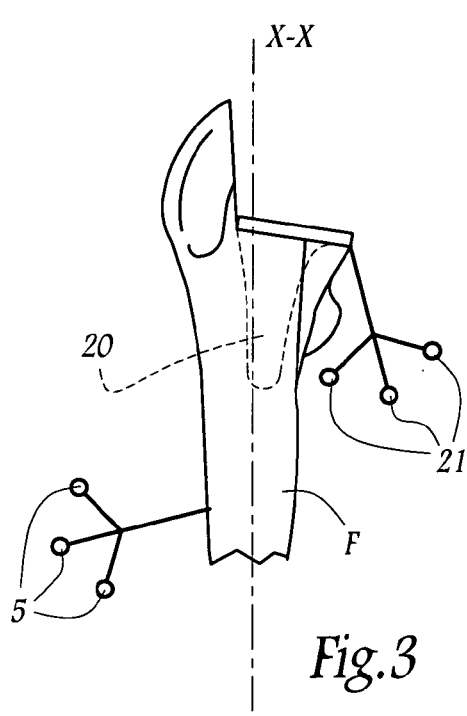
FIG. 3 is a schematic view in elevation of another part of the device according to the invention, during use on the femur of the patient's hip.

Referring now to the drawings, the surgical device 1 of FIG. 1 comprises a computer 2 associated with a unit for emitting and receiving infra-red radiations. This unit comprises a sensor 3 connected to the computer and a source of infra-red emission 4 covering the operative field in which is partly shown a hip of a patient to be treated. The hip comprises the upper part of a femur F and a corresponding part of the pelvic bone B.

In order to allow the computer 2 to locate the bones of the femur F and of the pelvis B in space, the device 1 comprises respective groups of markers 5 and 6 which passively return the infra-red radiation in the direction of the sensor 3. Each group of markers 5 or 6 forms a three-dimensional marking system allowing the computer 2/sensor 3 assembly to follow in space the respective displacements of the femur and pelvis. As the use of such markers is well known in the domain of orthopaedics, they will not be described here in greater detail.

Each group of markers 5 or 6 is fixed to the bone of the femur or pelvis by means of one or more rigid pins. As will be understood hereinafter, these pins are placed so as to leave the markers visible for the sensor 3 both when the articulation of the hip is reduced (as in FIG. 1) or when it is dislocated.

The computer 2 of the device 1 is also associated with one or more screens 7 adapted to display information useful for the surgeon, particularly the information relative to the position of the bones F and B and other data described hereinafter, preferably in the form of three-dimensional graphic representations as detailed hereinafter.

The device 1 also comprises control means 8, for example in the form of a pedal adapted to be actuated by the surgeon's foot.

The surgical device 1 further comprises other components which will be described in detail hereinafter in the description of a detailed example of use of the device with a view to implanting a total hip prosthesis 10 shown alone in FIG. 2. This prosthesis is constituted by a femoral part 11 to be implanted in the bone of the femur F and by a cotyloid part 12 to be implanted in the bone of the pelvis B. More precisely, the femoral part 11 comprises a stem 13 of longitudinal axis A-A, intended to be housed and retained in a diaphyseal cavity hollowed out in the medullary cavity of the femur F. The upper end of this stem extends, in a direction inclined with respect to axis A-A, in the form of a neck 14 at the free end of which is fixed a truncated spherical head 15, of axis of symmetry B-B and globally corresponding to the longitudinal axis of the neck 14.

The cotyloid part 12 comprises an acetabulum 16 in the form of a substantially hemispherical metallic cup intended to be connected to the bone of the pelvis B. C-C denotes the axis of revolution of the concave internal surface of the acetabulum 16. Inside this cup is provided to be fixedly housed a likewise hemispherical insert 17, of axis of revolution C-C, constituted by a plastics or ceramic material. The inner surface of the insert 17 is shaped in manner substantially complementary to the outer surface of the femoral head 15, so that the latter articulates in the manner of a ball-and-socket joint with respect to the cotyloid assembly 12.

The prosthesis 10 described hereinabove is given only by way of example and other prostheses, of different geometries and/or natures, may be implanted by means of the device 1 in accordance with the surgical method of implantation described hereinafter. In particular, the invention is applied to the fitting of prostheses of which the cotyloid part is constituted by one sole cup to be cemented on the bone of the pelvis and in which the prosthetic femoral head is directly articulated or of which the cotyloid part comprises, in addition to a first metal cup to be fixed to the pelvis, a second cup mounted in this first cup in articulated manner (in which case it is called a cotyloid assembly with double mobility). In any case, the cotyloid part of the prosthesis defines an axis of revolution for the concave inner surface of the cup to be fixed to the pelvis, similar to axis C-C.

In a first step, the surgeon incises the patient and collects a certain amount of data relative to the anatomical geometry of the bones of the femur F and of the pelvis B. To that end, different means for acquiring these data may be envisaged. By way of example, the surgeon uses a feeler 9 located by the computer 2/sensor 3 assembly and previously calibrated. This feeler 9 is passed over the noteworthy places of the bones and, at each of these positionings, the surgeon actuates the control pedal 8 so that the computer 2 records the position of the feeler 9 and consequently deduces the anatomical characteristics of the femur F and of the pelvis B. From these data and the tracking of the markers 5 and 6, the computer 2 is capable of locating in space the bones of the femur and of the pelvis.

During this data acquisition step, the articulation of the hip is successively dislocated and reduced, the reflecting markers 5 and 6 remaining visible for the sensor 3.

In a second step, the anatomical head of the femur F is, if necessary, resectioned.

In a third step, a cavity, intended subsequently to receive the femoral stem 13 of the prosthesis 10, is hollowed out in the diaphysis of the femur F. To that end, the surgeon firstly uses a rigid pin (not shown) which he introduces in the anatomical medullary cavity of the femur and which he marks in space by means of the computer 2/sensor 3 assembly by palpating for example one end of this pin bearing a predetermined relief. The surgeon then positions the pin thus marked so that it extends in a diaphyseal direction X-X intended to constitute the axis of implantation of the femoral part 11 of the prosthesis. This diaphyseal direction X-X is for example arbitrarily chosen by the surgeon as a function of the shape and state of the femur. When this pin is suitably positioned, the surgeon actuates the control pedal 8 and the computer 2 memorizes the position of axis X-X, particularly with respect to the femur F.

After having withdrawn the pin, the surgeon then uses a femoral rasp 20 shown in dotted lines in FIG. 3. This rasp 20 presents an active surface whose shape is substantially identical to the femoral stem 13. It is equipped with a group of reflecting markers 21, similar to markers 5 or 6, with the result that the computer 2/sensor 3 assembly makes it possible to display the position of the rasp with respect to the femur on the display screen 7. The surgeon thus employs this information to guide the rasp along axis X-X and to hollow out the desired femoral cavity.

At the end of the rasping step, the axis X-X of implantation of the femoral part 11 is replaced by the axis of rasping effectively made if the latter has moved away from the diaphyseal axis provided by the pin.

Figure 4:
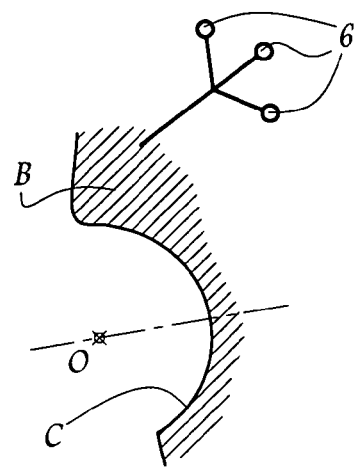
FIG. 4 is a view in section of a cotyloid cavity hollowed out in the pelvis of the patient's hip, by means of the device according to the invention.

In a fourth step, independent of the second and third steps described hereinbefore and which may therefore be inverted with these latter, a globally hemispherical cavity C is hollowed out in the zone of the pelvis B where the implantation of the acetabulum 16 of the prosthesis 10 is provided, as shown in FIG. 4. To allow the computer 2 to know the geometrical characteristics of the hollowed out cavity C, several solutions may be envisaged. A first solution consists in equipping the mill for hollowing out the cavity, with an assembly of reflecting markers similar to markers 5 or 6, so as to record the advance of this mill in the bone of the pelvis and thus allow the computer 2, which knows in advance the geometrical characteristics of the mill used, to determine in particular the position of the centre O of the milled cavity. Another solution, which may possibly be combined with the first, consists in palpating the cavity once it has been hollowed out. A third solution consists in using a phantom cup equipped with reflecting markers similar to markers 5 or 6 and in positioning this phantom cup at the bottom of the milled cavity.

In any case, at the end of this step, the computer knows the position in space of the centre O of the cavity C, as well, possibly, as other geometrical characteristics relative to this cavity, particularly its radius.

Figure 5:
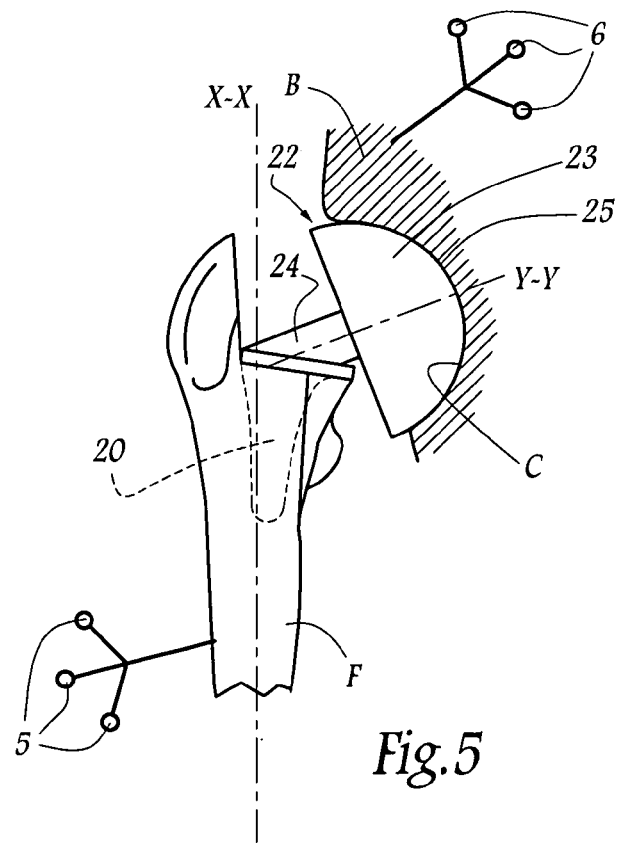
FIG. 5 is a schematic view illustrating the positioning, inside the cavity of FIG. 4, of a phantom femoral component of the device according to the invention.

In a fifth step, a plurality of configurations of articulation of the reduced hip of the patient are measured and memorized. To that end, a phantom femoral component 22 is used, shown in FIG. 5, presenting a shape globally similar to the upper end part of the femoral part 11 of the prosthesis 10, but with larger dimensions. More precisely, this femoral component 22, hereinafter referred to as "mega-head", comprises a substantially hemispherical head proper 23 with axis of symmetry Y-Y. The head 23 is fast with an essentially cylindrical neck 24 of axis Y-Y. The free end of the neck 24 is provided with means for connection to the upper free end of the rasp 20, left in place in the diaphysis of the femur F at the end of the rasping step.

The head 23 of the mega-head 22 defines an articular surface 25 substantially identical to the outer surface of the acetabulum 16 of the prosthesis 10 to be implanted. The head 23 is thus able to be articulated directly in the milled cavity C of the bone of the pelvis B. The position in space of the mega-head 22, particularly of its axis Y-Y, is known by the computer 2 via the sensors 5 since the mega-head is borne by the handle of the rasp 20 whose position with respect to the femur F has been determined and memorized by the computer during the third step of the operation.

While the mega-head 22 is articulated inside the cavity C, the surgeon manipulates the patient's hip so that it successively occupies a plurality of configurations considered as extreme, i.e. configurations that the local morphology of the patient imposes on him as natural limits. The patient's hip is thus manipulated into one or more configurations combining movements of flexion/extension, abduction/adduction and/or medial/lateral rotations, for example in the cross-legged configuration. Each of these extreme configurations characterizes an articular amplitude inherent in the hip of the patient operated on that the prosthesis 10 to be implanted is subsequently supposed to be able to reproduce without running the risk of being dislocated.

Figure 6:
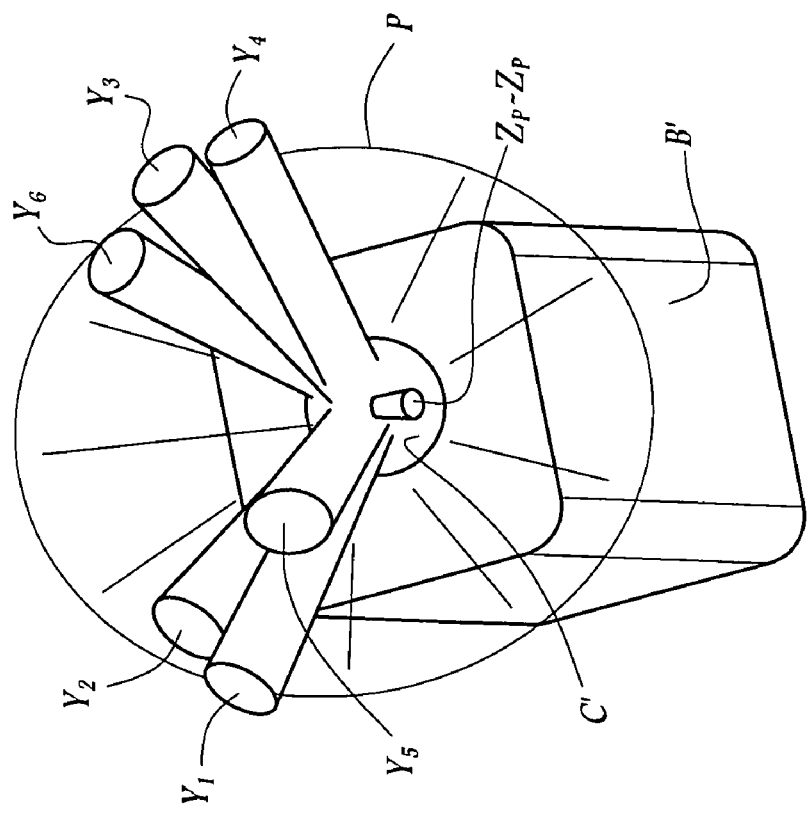
FIG. 6 shows a schematic view in perspective displayed for the surgeon's attention by the device according to the invention.

When the surgeon manipulates the hip joint in one of these extreme configurations, he actuates the control pedal 8 and the computer 2/sensor 3 assembly physically measures and memorizes the position of the axis Y-Y of the mega-head 22 with respect to the bone of the pelvis B. As shown in FIG. 6, the different positions thus really measured, for example six in number, are displayed on the screen 7, particularly in the form of symbolic bars $Y_1, Y_2, \ldots Y_6$, the pelvis B being schematically represented by a parallelepiped B' and the cavity for implantation C being represented by a corresponding, substantially hemispherical hollow C', the graphic representations of these elements B' and C' being a function of the prior measurements of the pelvis B and of the cavity C.

Once these measurements are effected, the hip joint is dislocated and the mega-head 22 is withdrawn.

Figure 7:
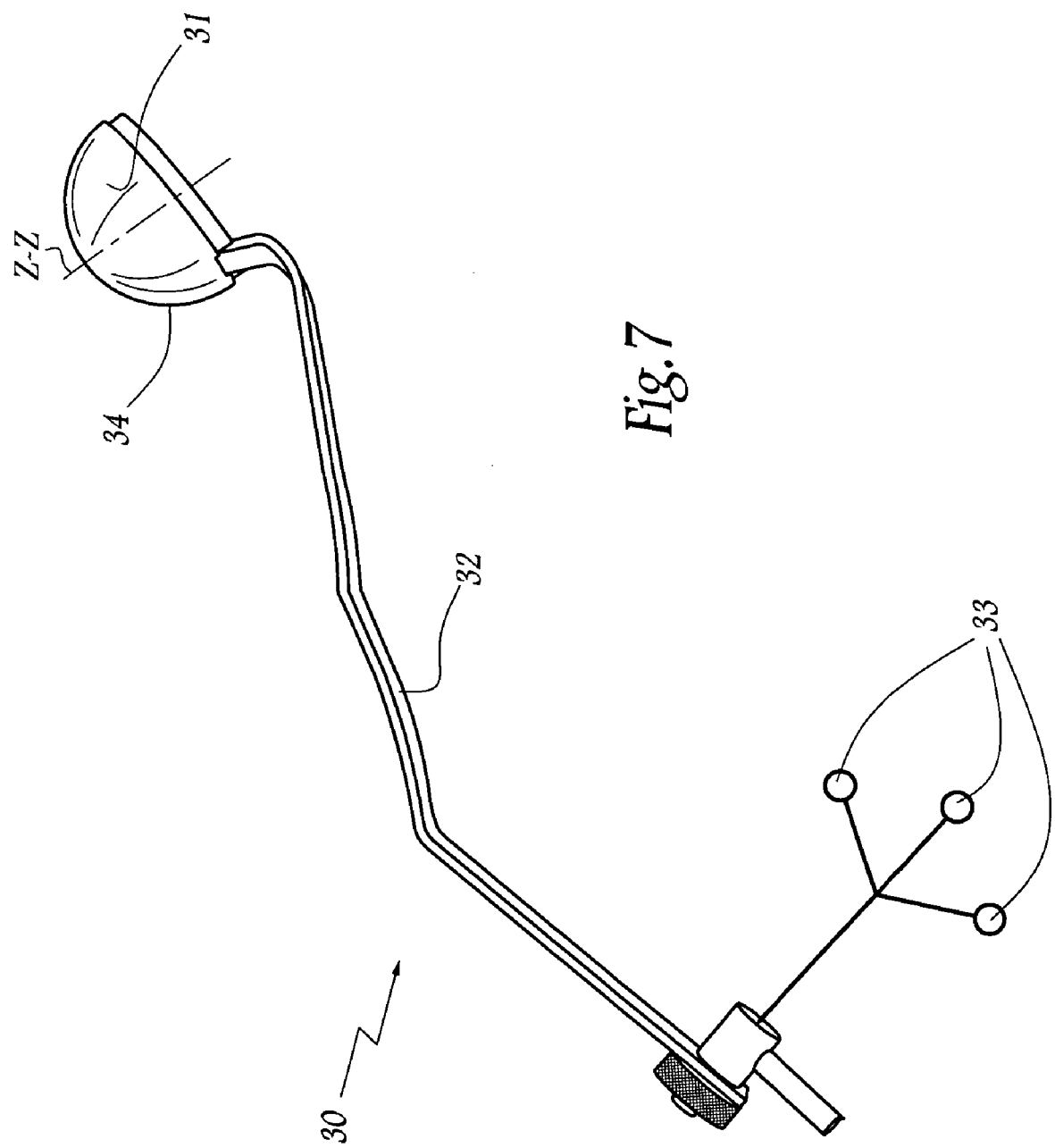
FIG. 7 is a view in perspective of a phantom cotyloid component of the device according to the invention.

In a sixth step, the surgeon uses a cotyloid ancillary tool 30 shown by itself in FIG. 7, which comprises a phantom acetabulum 31 fixedly connected to a rigid handle 32 for manipulation equipped with reflecting markers 33 similar to markers 5 or 6. The phantom acetabulum 31 is in the form of a hemisphere defining a convex articular surface 34 substantially identical to the outer surface of the acetabulum 16 of the prosthesis 10 to be implanted. The axis of generation of this phantom acetabulum is denoted Z-Z and is permanently marked in space by the computer 2/sensor 3 assembly, the computer knowing in advance the fixed geometrical relationship between this axis Z-Z and the markers 33.

By means of the handle 32, the phantom acetabulum 31 is manipulated so as to be housed in the milled cavity C so that its axis Z-Z passes substantially through the centre O of this cavity. As shown in FIG. 6, the computer 2 then displays on its screen 7, in superposition of the bars $Y_1$ to $Y_6$, the cone P of mobility of the prosthesis associated with the prosthesis 10 to be implanted, as a function of the position effectively occupied by the phantom acetabulum 31 in the cavity C, i.e. as a function of the position of its axis Z-Z. In effect, the computer 2 knows in advance the structural characteristics of the prosthesis 10, in particular the vertex angle of the cone of mobility of the prosthesis, only the position of the axis of revolution of this cone, simulated by the axis Z-Z of the phantom acetabulum 31, being adjustable by the surgeon.

The surgeon then visually compares the position of bars $Y_1$ to $Y_6$ representative of the maximum articular mobility of the patient's hip with the cone P of mobility of the prosthesis envisaged in the exact position of the phantom acetabulum 31 in the milled cavity C. If, as in FIG. 6, all the bars $Y_1$ to $Y_6$ appear, on the display screen 7, within the cone P, the position of the axis Z-Z is considered as acceptable, i.e. the prosthesis 10 thus implanted will allow the patient, from the point of view of prosthetic mobility, to limit as much as possible the risks of dislocations of the prosthesis. On the other hand, if one or more of the bars $Y_1$ to $Y_6$ lie outside the prosthetic cone P, the surgeon displaces the phantom acetabulum 31 until a position is found in which the risks of subsequent dislocations of the prosthesis 10 are considerably limited. To that end, complementary information on the respective angles of the bars $Y_1$ to $Y_6$ and of axis Z-Z may be furnished to the surgeon to allow him to find this position rapidly and easily. Moreover, other angles of view of the elements of FIG. 6 are advantageously proposed, particularly the angle at which the cone P globally appears in the form of a circle, the graphic representation of axis Z-Z in that case being directed perpendicularly to the plan of view.

When the surgeon has found a satisfactory position for the phantom acetabulum 31, he records the position of its axis Z-Z by means of the computer 2, this direction, denoted $Z_p$-$Z_p$ in FIG. 6, in that case being chosen as the preferential direction for subsequently implanting the cotyloid part 12 of the prosthesis 10.

Optionally, parallel to or after the determination of the preferential direction of axis Z-Z, it is possible to monitor this direction by equipping the rasp 20 with a test femoral head (not shown), with geometrical dimensions substantially identical to the femoral head 15 of the prosthesis 10. This test head is then able to be articulated inside the phantom acetabulum 31 which reproduces the internal geometrical characteristics of the insert 17 of the prosthesis 10. The hip joint thus formed is in that case reduced then manipulated by the surgeon in different extreme articular configurations, in order to verify in particular that the neck of the test head does not come into contact with the osseous matter of the pelvis B, provoking the dislocation of the prosthesis.

Figure 8:
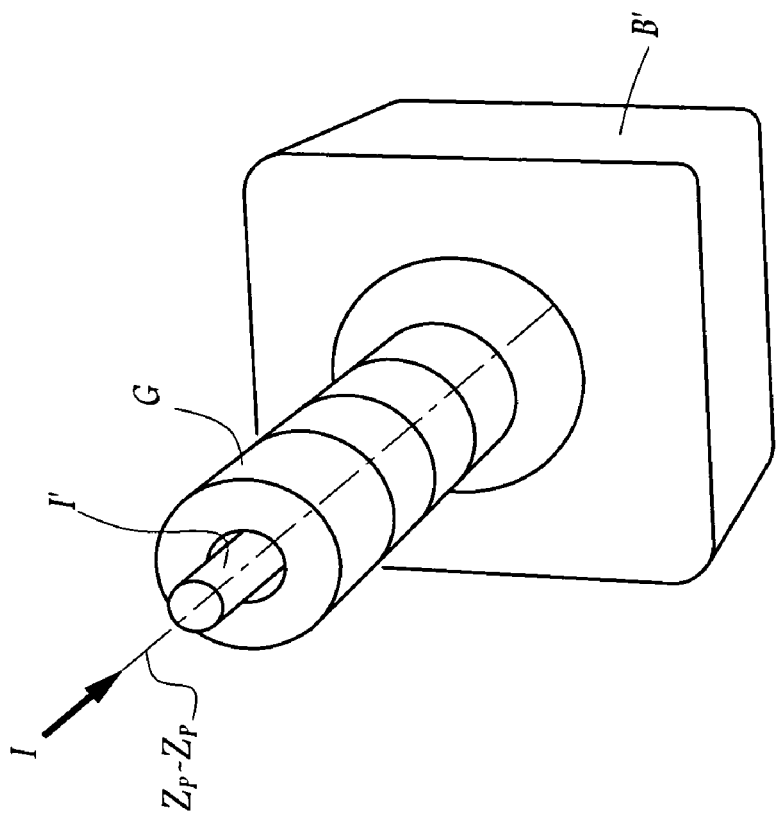
FIG. 8 shows another schematic view in perspective displayed for the surgeon's attention by the device according to the invention.

After having withdrawn the phantom acetabulum 31, the surgeon then uses, in a seventh step, an impactor (not shown) to definitively place the acetabulum 16 of the prosthesis 10 in position. To enable this acetabulum to be impacted so that its axis C-C merges with the preferential direction $Z_p$-$Z_p$, this ancillary tool is equipped with means for marking in space allowing the computer 2/sensor 3 assembly to display on the screen 7 the position of its direction of impaction I, as shown in FIG. 8 in which the impactor is symbolized by a tube I'. Before applying the effort of impaction on the acetabulum 16, the surgeon positions the impactor so that the direction I, in line with axis C-C of the acetabulum, is substantially aligned with the preferential position $Z_p$-$Z_p$ of the axis of the cone of mobility of the prosthesis. To that end, the computer 2 displays a virtual guiding tube G, partially hollowed out, inside which the symbolic representation I' of the impactor must be placed coaxially in order to ensure alignment of the directions I and $Z_p$-$Z_p$. A visual signal, such as a change of colour or a flashing, indicates the alignment to the surgeon.

The insert 17 is then housed in the implanted acetabulum.

Once the impaction is effected, all the femoral components of the device 1 are withdrawn and the femoral part 11 of the prosthesis 10 is, in an eighth step, implanted so that the axis A-A of its stem 13 substantially merges with the axis of femoral implantation X-X. Insofar as the rasp 20 has made a diaphyseal cavity substantially complementary of this stem, it suffices to impact the stem 13 in the femur F in conventional manner in order to obtain merging of the axes A-A and X-X.

The device 1 according to the invention thus enables the prosthesis 10 to be positioned in optimum manner in order to reproduce as best possible the kinematic capacities of the anatomical hip of the patient operated on. It will be noted that the eight per-operative steps described hereinabove are carried out during a surgical operation proper, i.e. during which the patient is for example under anaesthetics.

Moreover, the different data recorded during the fit of the prosthesis 10 may be used for making a post-operative check-up and thus enable the articular capacities of the prosthesis in its state of implantation in the hip bones to be characterized with precision. It is also possible to determine the elongation between the femur F and the pelvis B during the surgical operation. However, it will be noted that the data acquired are clearly less numerous than those necessary for the functioning of a biomechanical simulator of the hip to be operated on and the corresponding data processing means of the device according to the invention are therefore less expensive and less complex to manipulate.

As indicated hereinabove, the implantation device 1 is, in addition, easily applicable to prostheses of different geometries, only the characteristics of prosthetic mobility having to be furnished to the computer 2 to allow the cone P to be displayed. Corresponding sets of mills and rasps are provided, as well as a set of a plurality of phantom acetabula 31 of different sizes and geometries, adapted to be connected to the same handle 32.

Various arrangements and variants of the implantation device 1 described hereinabove may in addition be envisaged.

In particular, the use of the cotyloid ancillary tool 30 is not indispensable since the data relative to the cone P of mobility of the prosthesis are known by the computer 2 in advance, only the position of the axis Z-Z with respect to the cavity C of the pelvis B having to be adjusted during the operation in order to guarantee subsequent functioning without dislocation of the prosthesis 10. It may therefore be envisaged that the surgeon use only virtual representations to adjust the position of this axis Z-Z, by displaying the different cones of mobility of the prosthesis which correspond to different positions of the axis Z-Z, for example by means of an appropriate computer interface allowing it to modify the position of the virtual axis Z-Z and to choose the preferential axis $Z_p$-$Z_p$.

Other variants are set forth hereinbelow:
to support the mega-head 22, the rasp handle 20 may be replaced by a femoral pin or by the femoral stem of the prosthesis to be implanted, in which case the mega-head is possibly integral with its femoral support,
the mega-head 22 described hereinabove may be replaced by a phantom femoral component constituted by a head whose dimensions are substantially identical to those of the prosthetic femoral head and by a hemispherical dome articulated on this head, whose dimensions are substantially identical to those of the prosthetic cotyloid part,
the means for locating the bones of the femur F and of the pelvis B are not limited to markers reflecting the infrared, it being possible to use, for example, markers sensitive to ultra-sounds or to the electromagnetic fields,
the cavity C may be milled after having determined the preferential direction $Z_p$-$Z_p$; in that case, the anatomical cavity of the hip is used as articular housing for the mega-head 22 in order to measure the different extreme articular configurations,
means other than a display screen may be envisaged for communicating to the surgeon a return of information on the comparison between the measurements of the extreme articular configurations and the cone of mobility of the prosthesis; sound or touch indications may thus inform the surgeon as to the state of this comparison and guide him in the determination of the preferential direction $Z_p$-$Z_p$, and/or
the determination of the preferential direction Z-Z may be integrally ensured by an appropriate software equipping the computer 2, from the comparison of the cone P and the measurements of the different extreme articular configurations measured per-operatively, and this by calculation and extrapolation.

What is claimed is:

1. Surgical method for implantation of a total hip prosthesis, in which, per-operatively and successively:
locating in space a bone of a femur and a bone of a pelvis of a patient to be treated;
memorizing with a computer a plurality of measured positions of a given femoral prosthetic direction with respect to a cavity of the pelvis prior to positioning an acetabular component of the prosthesis in the cavity, the acetabular component having a predetermined cone of mobility defining an axis of revolution;
determining at least one preferential position of the axis of revolution of the acetabular component without having to assemble the total hip prosthesis by comparing the measured positions of the femoral prosthetic direction with the predetermined cone of mobility and adjusting the position of the axis of revolution of the cone of mobility with respect to the cavity in the course of the surgical operation until the measured positions of the given femoral prosthetic direction are all located within the predetermined cone of mobility of the acetabular component; and
impacting the acetabular component of the prosthesis in the cavity of the pelvis in the preferential position.

2. A surgical method for replacing an anatomical ball-and-socket joint with a prosthetic ball-and-socket joint having a first portion and a second portion, one of the first and second portions corresponding to a ball portion of the ball-and-socket joint and the other of the first and second portions corresponding to a socket portion of the ball-and-socket joint, the method comprising per-operatively performing the steps of:
locating the anatomical ball-and-socket joint in space;
removing at least a portion of the anatomical ball-and-socket joint;
engaging at least a first portion of the prosthetic ball-and-socket joint or a phantom prosthetic ball-and-socket joint with a corresponding portion of the anatomical ball-and-socket joint;
articulating the first portion of the prosthetic ball-and-socket joint or the phantom prosthetic ball-and-socket joint through a plurality of configurations corresponding generally to natural limits of the anatomical ball-and-socket joint and recording in a computer the natural limits;
disengaging the first portion of the prosthetic ball-and-socket joint or the phantom prosthetic ball-and-socket joint from the corresponding portion of the anatomical ball-and-socket joint;
superimposing in the computer the natural limits of the anatomical ball-and-socket joint with a predetermined cone of mobility defined by a second portion of the prosthetic ball-and-socket joint before implanting the second portion of the prosthetic ball-and-socket joint and adjusting an axis of revolution of the predetermined cone of mobility with respect to the anatomical ball-and-socket joint until the recorded natural limits are all positioned within the predetermined cone of mobility prior to implanting the prosthetic ball-and-socket joint in order to determine an optimum position of the prosthetic ball-and-socket joint; and
implanting the prosthetic ball-and-socket joint in the optimum position.

3. The method of claim 2 wherein the anatomical ball-and-socket joint comprises a hip joint and removing at least a portion of the anatomical ball-and-socket joint comprises removing at least a portion of a femoral head.

4. The method of claim 3 further comprising recording in the computer a femoral axis of an anatomical medullary cavity of a femur.

5. The method of claim 3 further comprising using the computer to guide a femoral rasp along a femoral axis.

6. The method of claim 2 further comprising:
hollowing out an anatomical socket portion of the anatomical ball-and-socket joint; and
recording geometric characteristics of the hollowed out anatomical socket portion.

7. The method of claim 2 further comprising:
hollowing out an anatomical socket portion of the anatomical ball-and-socket joint;
per-operatively articulating a phantom prosthetic ball portion in the anatomical socket portion; and
recording the natural limits of the anatomical ball-and-socket joint.

8. The method of claim 2 further comprising recording in the computer a center of an anatomical socket portion of the anatomical ball-and-socket joint.

9. The method of claim 2 further comprising recording in the computer an axis of symmetry for an anatomical socket portion of the anatomical ball-and-socket joint.

10. The method of claim 2 wherein engaging at least the first portion of the prosthetic ball-and-socket joint or the phantom prosthetic ball-and-socket joint with the corresponding portion of the anatomical ball-and-socket joint comprises:
engaging a phantom prosthetic ball-and-socket joint with a portion of the anatomical ball-and-socket joint;
per-operatively articulating the phantom prosthetic ball-and-socket joint through a plurality of configurations corresponding generally to the natural limits of the anatomical ball-and-socket joint and recording in the computer the natural limits; and
removing the phantom prosthetic ball-and-socket joint before implanting the prosthetic ball-and-socket joint.

11. The method of claim 2 further comprising:
engaging a phantom prosthetic ball portion with an anatomical socket portion;
per-operatively articulating the phantom prosthetic ball portion in the anatomical socket portion to the natural limits of one or more of flexion/extension, abduction/adduction, and medial/lateral rotation; and
recording in the computer the natural limits.

12. The method of claim 2 further comprising:
engaging a phantom prosthetic ball portion with an anatomical socket portion; and
aligning an axis of symmetry of the phantom prosthetic ball portion with an axis of symmetry of the anatomical socket portion.

13. The method of claim 2 further comprising:
engaging a phantom prosthetic ball portion with an anatomical socket portion;
aligning the phantom prosthetic ball portion with the cone of mobility; and
superimposing the cone of mobility on an axis of symmetry of the phantom prosthetic ball portion.

14. The method of claim 2 further comprising communicating to a surgeon a comparison of the cone of mobility to the natural limits.

15. The method of claim 2 further comprising:
aligning an axis of symmetry of a prosthetic ball portion with an axis of symmetry of an anatomical socket portion; and
implanting the prosthetic ball portion in the anatomical socket portion.

16. The method of claim 2 further comprising implanting the prosthetic ball-and-socket joint within the natural limits of the anatomical ball-and-socket joint.

17. The method of claim 2 further comprising:
comparing the cone of mobility with the natural limits; and
identifying a preferential axis of implantation.

18. The method of claim 17 further comprising:
aligning an axis of symmetry of a prosthetic ball portion with the preferential axis of implantation; and
implanting the prosthetic ball portion in the anatomical socket portion so that an axis of symmetry of the prosthetic ball portion is generally merged with the preferential axis of implantation.

19. The method of claim 2 wherein superimposing in the computer the natural limits of the anatomical ball-and-socket joint with the cone of mobility of the prosthetic ball-and-socket joint occurs per-operatively.

20. A surgical method for replacing an anatomical ball-and-socket joint with a prosthetic ball-and-socket joint, the method comprising per-operatively:
locating the anatomical ball-and-socket joint in space;
removing at least a portion of the anatomical ball-and-socket joint;
engaging at least a first portion of the prosthetic ball-and-socket joint or a phantom prosthetic ball-and-socket joint with a corresponding portion of the anatomical ball-and-socket joint;
articulating the prosthetic ball-and-socket joint or the phantom prosthetic ball-and-socket joint through a plurality of configurations corresponding generally to natural limits of the anatomical ball-and-socket joint and recording in a computer the natural limits;
after recording the natural limits, engaging at least a second portion of the prosthetic ball-and-socket joint or the phantom prosthetic ball-and-socket with a corresponding portion of the anatomical ball-and-socket joint;
superimposing in the computer the natural limits of the anatomical ball-and-socket joint with a predetermined cone of mobility of the prosthetic ball-and-socket joint having a known axis of revolution corresponding to a position of the second portion of the prosthetic ball-and-socket joint;
identifying a preferential axis of implantation prior to implanting the anatomical ball-and-socket joint by adjusting the position of the second portion of the prosthetic ball-and-socket joint until the superimposition indicates the natural limits are positioned entirely within the cone of mobility; and
implanting the prosthetic ball-and-socket joint generally along the preferential axis of implantation.

21. A surgical method for replacing an anatomical ball-and-socket joint with a prosthetic ball-and-socket joint, where the anatomical ball-and-socket joint includes ball anatomy and socket anatomy, the prosthetic ball-and-socket joint has a predetermined cone of mobility and includes a prosthetic ball portion and a prosthetic socket portion, and the method comprises:
determining a maximum desired articular mobility of the prosthetic ball-and-socket joint, including:
securing a ball part relative to a portion of the ball anatomy,
forming a cavity in the socket anatomy,
engaging the ball part in the cavity of the socket anatomy,
articulating the ball part through a plurality of configurations corresponding generally to natural limits of the anatomical ball-and-socket joint to define the maximum desired articular mobility of the prosthetic ball-and-socket joint, and
removing the ball part from the cavity;
determining an implant position for the prosthetic socket portion in the cavity, including:
comparing the maximum desired articular mobility of the prosthetic ball-and-socket joint and the cone of mobility of the prosthetic ball-and-socket joint using a computer, the cone of mobility having an axis of rotation that is adjustable according to a position of the prosthetic socket portion, and
locating a preferred position for the prosthetic socket portion using the computer and without assembling the prosthetic ball-and-socket joint by selecting a position for the axis of rotation of the cone of mobility relative to the maximum desired articular mobility where the maximum desired articular mobility of the prosthetic ball-and-socket joint is located entirely within the cone of mobility of the prosthetic ball-and-socket joint; and
securing the prosthetic socket portion at the implant position and engaging the prosthetic ball portion with the prosthetic socket portion.

22. The method of claim 21, wherein optimizing the desired articular mobility relative to the cone of mobility includes visualizing the superimposition of the desired articular mobility and cone of mobility as the position of the axis of rotation is changed.

23. The method of claim 21, wherein the ball anatomy is a femur, the ball part is a phantom femoral component, the prosthetic ball part is a final femoral component, and the method further comprises removing the phantom femoral component after determining the axis of rotation and the desired articular mobility, and securing the final femoral component of the ball-and-socket joint to the femur.

24. The method of claim 21, wherein the ball anatomy is a femur, the socket anatomy is a pelvis, and the method further comprises milling a cavity in the pelvis, inserting the first ball part in the cavity before securing the prosthetic socket portion in the cavity, and determining the maximum desired articular mobility and the direction of an axis of rotation of the prosthetic ball-and-socket joint by articulating the ball part through a plurality of configurations corresponding generally to natural limits of the anatomical ball-and-socket joint.

* * * * *